(12) United States Patent
Wang

(10) Patent No.: US 8,783,863 B2
(45) Date of Patent: Jul. 22, 2014

(54) CONTACT LENS FOR MYOPIA CONTROL

(75) Inventor: Chung Lin Wang, Taichung (TW)

(73) Assignee: Largan Medical Co., Ltd., Taichung (TW)

(*) Notice: Subject to any disclaimer, the term of this patent is extended or adjusted under 35 U.S.C. 154(b) by 65 days.

(21) Appl. No.: 13/604,130

(22) Filed: Sep. 5, 2012

(65) Prior Publication Data

US 2013/0293834 A1 Nov. 7, 2013

(30) Foreign Application Priority Data

May 7, 2012 (TW) .............................. 101116147 A

(51) Int. Cl.
*G02C 7/04* (2006.01)

(52) U.S. Cl.
CPC ...................................... *G02C 7/044* (2013.01)
USPC ................................ 351/159.13; 351/159.37

(58) Field of Classification Search
CPC .......... G02C 7/04; G02C 7/041; G02C 7/042; G02C 7/044; G02C 7/045
USPC ............... 351/159.02, 159.05, 159.06, 159.1, 351/159.11, 159.12, 159.13, 159.14, 159.2, 351/159.37

See application file for complete search history.

(56) References Cited

U.S. PATENT DOCUMENTS

2007/0296916 A1* 12/2007 Holden et al. ................ 351/161

* cited by examiner

*Primary Examiner* — Darryl J Collins
*Assistant Examiner* — Gary O'Neill
(74) *Attorney, Agent, or Firm* — Morris, Manning & Martin, LLP; Tim Tingkang Xia, Esq.

(57) ABSTRACT

This invention provides a contact lens for myopia control comprising: an object-side surface comprising a central zone, a transition zone and a peripheral zone which are concentric and have different refractive power, at least one of the three zones being aspheric; and an image-side surface; wherein the central zone provides correction power to focus a foveal image on the retina, the peripheral zone provides a myopic defocus effect by generating a para-fovea image in front of the retina, and the transition zone with one or more focuses provides a refractive power in diopter (D) ranging from +0.25 D to +8.00 D.

6 Claims, 3 Drawing Sheets

CONTACT LENS FOR MYOPIA CONTROL

CROSS-REFERENCE TO RELATED APPLICATION

This non-provisional application claims priority under 35 U.S.C. §119(a) on Patent Application No. 101116147 filed in Taiwan (R.O.C.) on May 7, 2012, the entire contents of which are hereby incorporated by reference.

BACKGROUND OF THE INVENTION

1. Field of the Invention

The present invention relates to a contact lens capable of simultaneously correcting myopia and suppressing the progression of myopia.

2. Description of the Prior Art

Regarding a conventional contact lens, the correction power is provided by the central zone of the lens only. The peripheral zone of the lens does not provide correction power and is designed such that the contact lens has a shape conforming to the shape of the eyeball and can be worn easily. FIG. 1 is a schematic representation illustrating the image formation of a conventional contact lens 110. After a parallel light beam has passed through the conventional contact lens 110, the central zone of the conventional contact lens 110 forms a central-zone focus 01 right on the retina while the peripheral zone of the conventional contact lens 110 forms a peripheral-zone focus 02 behind the retina because the peripheral zone of the conventional contact lens 110 does not provide correction power. Current researches show that the growth of the eyeball can be effectively suppressed to slow the progression of myopia if the peripheral-zone focus 02 image is formed in the front of the retina by a myopic defocus effect. FIG. 2 is a schematic representation illustrating the image formation of a conventional contact lens 210 for myopia control. After a parallel light beam has passed through the conventional contact lens 210 for myopia control, a central-zone focus 01 is formed on the retina while a peripheral-zone focus 02 is formed in front of the retina to achieve the effect of myopia control. However, as the focuses of the two zones are distantly formed, the wearer may feel uncomfortable and be less tempted to wear such contact lenses.

SUMMARY OF THE INVENTION

This invention provides a contact lens for myopia control comprising: an object-side surface comprising a central zone, a transition zone, and a peripheral zone, the three zones being concentric and at least one of which being aspheric; and an image-side surface; wherein the central zone has an outer radius ranging from 0.5 to 2.6 mm, the transition zone comprises an inner radius the same as the outer radius of the central zone and an outer radius ranging from 1 to 3.9 mm, the peripheral zone comprises an inner radius the same as the outer radius of the transition zone and an outer radius ranging from 3 to 7.7 mm, and the transition zone with one or more focuses provides refractive power in diopter (D) ranging from +0.25 D to +8.00 D.

In the aforementioned contact lens for myopia control of the present invention, the outer radius of the central zone is defined as R1, the outer radius of the transition zone is defined as R3, and they preferably satisfy a relation of In the aforementioned contact lens, the central zone can present a clear image in the fovea and the peripheral zone can provides myopic defocus effect by generating one or more para-fovea images. The arrangement of the two zones enables the contact lens to simultaneously correct myopia and suppress the progression of myopia. Moreover, the transition zone presents one or more images on or in front of the retina to serve as a buffer for images presented by the central zone and the peripheral zone, thereby relieving the wearer of any discomfort in wearing the contact lens.

BRIEF DESCRIPTION OF THE DRAWINGS

FIG. 4 is a schematic representation of the contact lens for myopia control in accordance with the present invention, wherein FIG. 4A is a schematic representation of an object-side surface of the contact lens for myopia control and FIG. 4B is a sectional view of the contact lens for myopia control taken along the line I-I' in FIG. 4A.

DETAILED DESCRIPTION OF THE PREFERRED EMBODIMENTS

Figure 1:
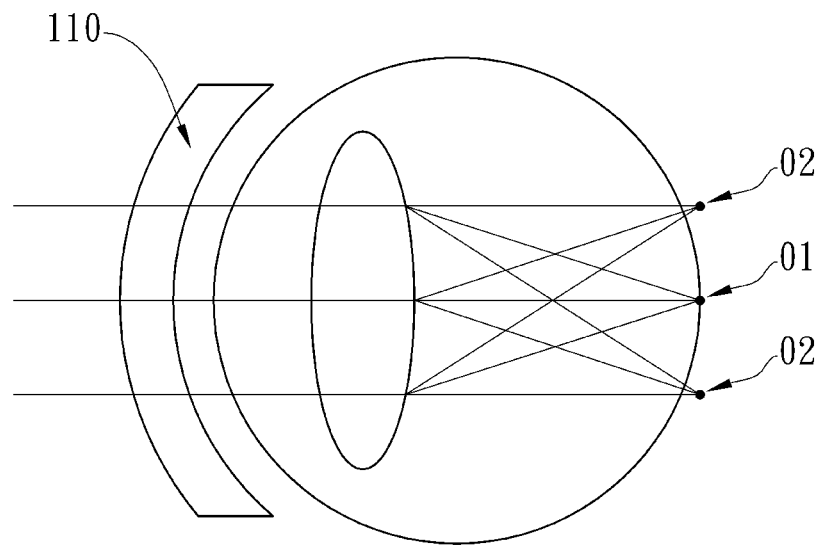
FIG. 1 is a schematic representation illustrating the relative positions of the focuses formed by the respective zones of a prior art contact lens.
Figure 2:
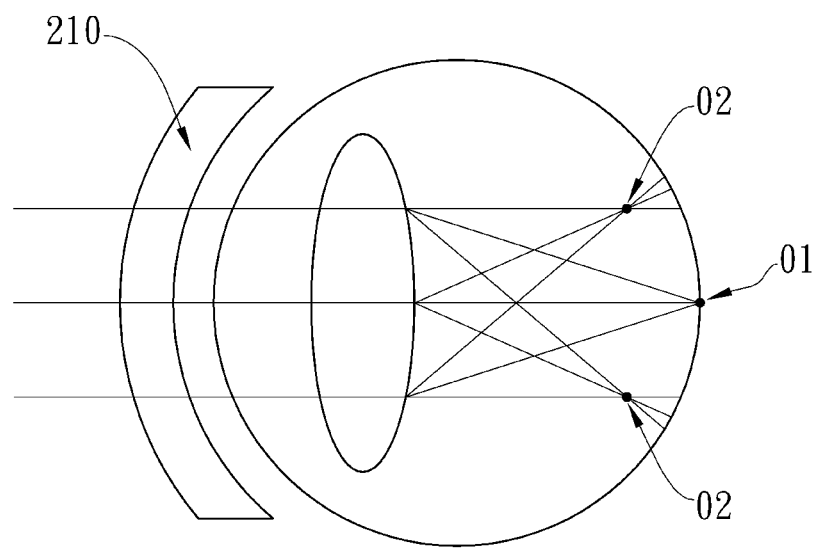
FIG. 2 is a schematic representation illustrating the positions of the focuses formed by the respective zones of a prior art contact lens for myopia control.

The term "central zone" of the present invention refers to a region of the contact lens configured to correct the central vision; the term "peripheral zone" refers to a region of the contact lens configured to correct the peripheral vision; the term "transition zone" refers to a region of the contact lens configured to connect "central zone" and "peripheral zone". In the present invention, the term "fovea" refers to a region located in the center of the retina and responsible for central vision; the term "para-fovea" refers to a region located outside the fovea and responsible for the peripheral vision. While the reference numerals 01, 02 and 03 in the appended drawings illustrate the relative relation among the focuses of respective zones, each zone of the contact lens is not limited to have only one focus.

Figure 4:
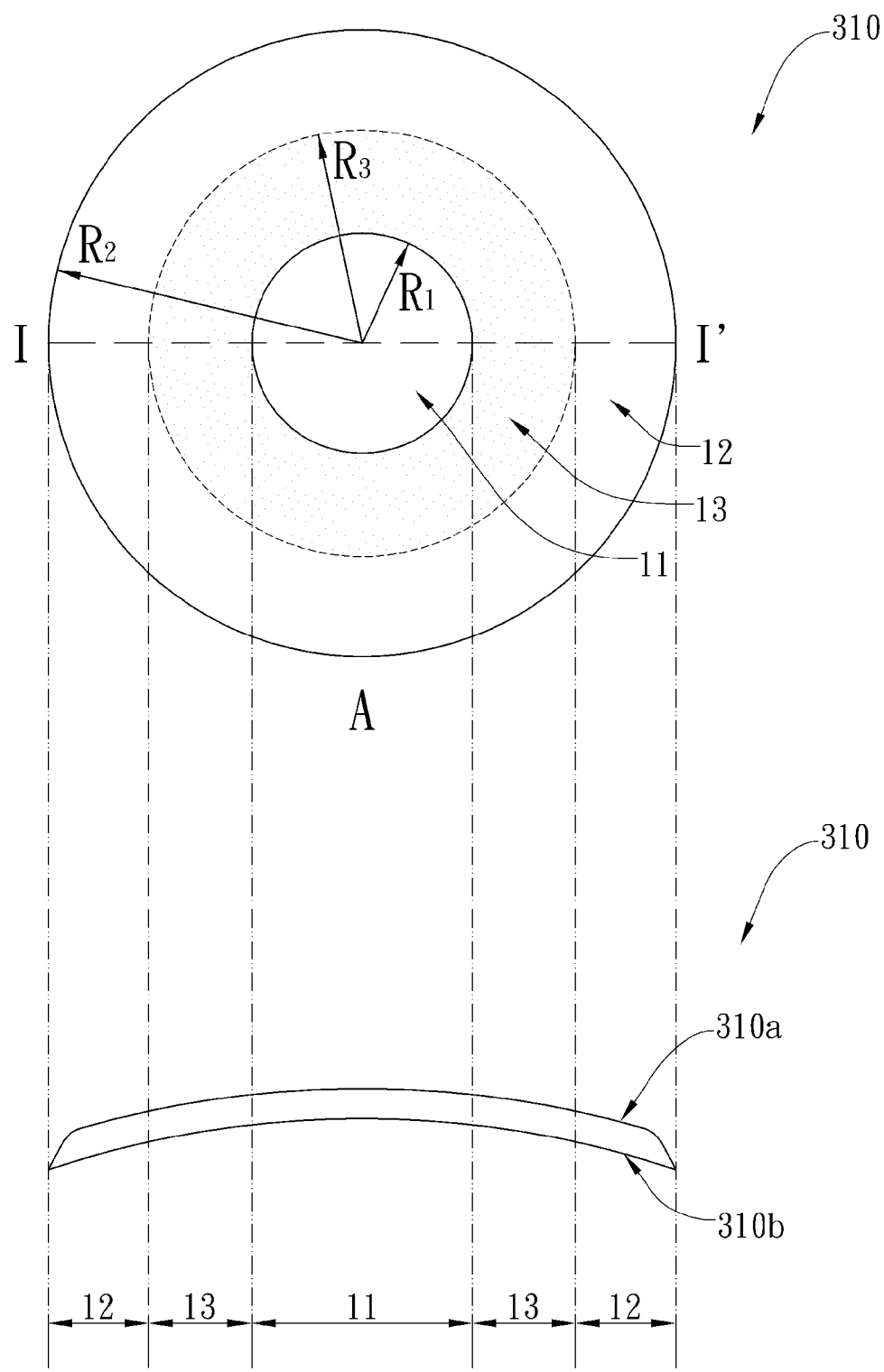

FIG. 4 is a schematic representation of the contact lens 310 for myopia control in accordance with the present invention, wherein FIG. 4A is a schematic representation of an object-side surface 310a of a contact lens 310 for myopia control in accordance with the present invention. The object-side surface 310a comprises a central zone 11, a transition zone 13 and a peripheral zone 12 which are concentric and connected in a sequential order. The central zone 11 has an outer radius R1 ranging from 0.5 to 2.6 mm; the transition zone 13 comprises an outer radius R3 ranging from 1 to 3.9 mm; the peripheral zone 12 comprises an outer radius R2 ranging from 3 to 7.7 mm. The contact lens further comprises an image-side surface 310b which is in contact with the eyeball of the wearer. FIG. 4B is a sectional view of the contact lens 310 taken along the line I-I'. The aforementioned three zones have different refractive powers, wherein the transition zone 13 can provide a plurality of refractive powers in diopter (D) ranging from +0.25 D to +8.00 D.

In an embodiment of the present invention, the contact lens has a thickness of 0.06 mm, a moisture content of 57%, and an expansion coefficient of 1.288 in the hydrated state. Moreover, the contact lens in the hydrated state has a refractive index of 1.404. When the contact lens is in the pre-hydrated state, the outer radii of the three zones thereof are as follows:

R1=1.15 mm, R2=5.49 mm, R3=2.4 mm. As the contact lens in the hydrated state has an expansion coefficient of 1.288, the radii of the outer circles of the three zones thereof change as follows: R1=1.48 mm, R2=7.07 mm, R3=3.09 mm.

In the contact lens of the aforementioned embodiment of the present invention, the image-side surface 310$b$ thereof has a curvature radius of 6.5 mm. The central zone 11 of the object-side surface 310$a$ of the contact lens has a curvature radius of 6.81 mm and provides refractive power in diopter (D) of −2.0 D; the transition zone 13 has five different curvature radii, which are 6.72 mm, 6.63 mm, 6.53 mm, 6.44 mm and 6.35 mm, respectively, in a direction from the central zone 11 to the peripheral zone 12, and provides refractive power in diopter (D) within a range of +3.0 D (−2.0 D~+1.0 D) between the central zone 11 and peripheral zone 12. While the transition zone 13 of the embodiment is divided into five small regions according to the five different curvature radii (6.72 mm, 6.63 mm, 6.53 mm, 6.44 mm and 6.35 mm), it can actually be divided into infinite number of small regions with different radii of curvature according to the needs.

Figure 3:
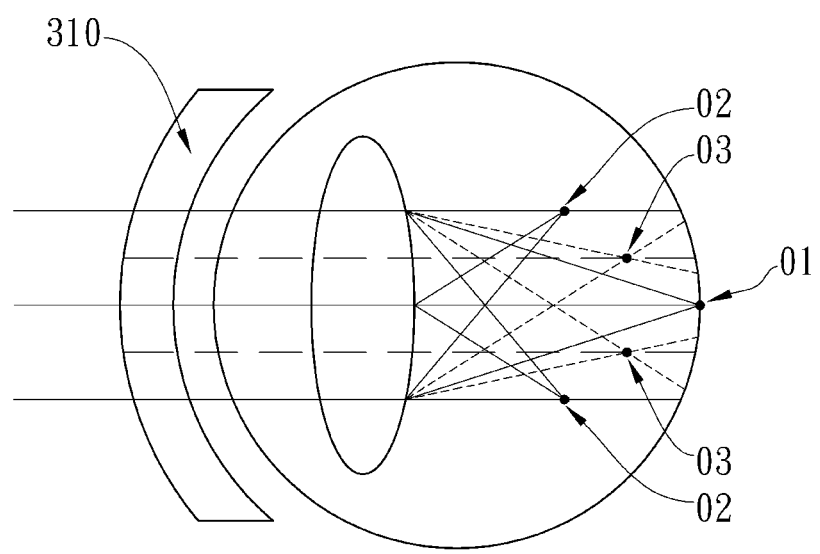
FIG. 3 is a schematic representation illustrating the relative positions of the focuses formed by the respective zones of a contact lens for myopia control in accordance with the present invention.

The contact lens 310 for myopia control of the present invention provides different refractive powers to adjust the positions of the focuses for different regions of the retina. FIG. 3 is a schematic representation illustrating the relative positions of the focuses which has been corrected by different regions of the contact lens 310. The central zone 11 adjusts the position of the focus for the fovea so that the central-zone focus 01 is formed right on the retina to present a clear image; the peripheral zone 12 adjusts the position of the focus for the para-fovea so that the peripheral-zone focus 02 is formed in front of the retina to present a defocused image and thereby to suppress the growth of the eyeball and suppress the progression of myopia; the transition zone 13 adjusts the position of the focus for a region between the fovea and the para-fovea. The transition zone 13 with a plurality of refractive powers generates a plurality of focuses for the region between the fovea and the para-fovea, and the plurality of focuses are formed on or in front of the retina. The transition zone 13 is configured to provide refractive power in diopter (D) ranging from +0.25 D to +8.00 D. In other words, the transition zone 13 presents one or more images on or in front of the retina to serve as a buffer for the images presented by the central zone 11 and the peripheral zone 12, thereby relieving the wearer of any discomfort in wearing the contact lenses.

What is claimed is:

1. A contact lens for myopia control comprising:
   an object-side surface comprising a central zone, a transition zone, and a peripheral zone which are concentric and connected in a sequential order, the three zones having different refractive power and at least one of which being aspheric; and
   an image-side surface,
   wherein the central zone has an outer radius the same as an inner radius of the transition zone, the transition zone has an outer radius the same as an inner radius of the peripheral zone;
   wherein the transition zone with one or more focuses provides refractive power in diopter (D) ranging from +0.25 D to +8.00 D; and
   wherein the peripheral zone has an outer radius ranging from 5.49 to 7.7 mm.

2. The contact lens for myopia control according to claim 1, wherein the central zone has an outer radius ranging from 0.5 to 2.6 mm.

3. The contact lens for myopia control according to claim 1, wherein the transition zone has an inner radius ranging from 0.5 to 2.6 mm and an outer radius ranging from 1 to 3.9 mm.

4. The contact lens for myopia control according to claim 1, wherein the peripheral zone has an inner radius ranging from 1 to 3.9 mm.

5. The contact lens for myopia control according to claim 1, wherein the outer radius of the central zone is R1, the outer radius of the transition zone is R3, and they satisfy a relation of 1<R3/R1<5.

6. A contact lens for myopia control comprising:
   a central zone having an outer radius ranging from 0.5 to 2.6 mm;
   a transition zone whose inner radius is the same as the outer radius of the central zone and whose outer radius is ranging from 1 to 3.9 mm; and
   a peripheral zone whose inner radius is the same as the outer radius of the transition zone and whose outer radius is ranging from 5.49 to 7.7 mm,
   wherein the three zones are concentric and connected in a sequential order, and the three zones have different refractive power and at least one of which is aspheric; and
   wherein the central zone provides correction power to focus a foveal image on the retina, the transition zone with one or more focuses provides refractive power in diopter (D) ranging from +0.25 D to +8.00 D and thereby to focus images between the fovea and the para-fovea on or in front of the retina, and the peripheral zone provides a myopic defocus effect by generating a para-fovea image in front of the retina.

* * * * *